United States Patent [19]

Stendel et al.

[11] Patent Number: 5,059,593
[45] Date of Patent: Oct. 22, 1991

[54] POUR-ON FORMULATIONS WHICH ARE ACTIVE AGAINST TICKS

[75] Inventors: Wilhelm Stendel, Wuppertal; Herbert Voege, Leverkusen, both of Fed. Rep. of Germany

[73] Assignee: Bayer Aktiengesellschaft, Leverkusen, Fed. Rep. of Germany

[21] Appl. No.: 508,389

[22] Filed: Apr. 11, 1990

Related U.S. Application Data

[63] Continuation of Ser. No. 821,088, Jan. 21, 1986, abandoned, which is a continuation of Ser. No. 595,083, Mar. 30, 1984, abandoned, which is a continuation of Ser. No. 281,616, Jul. 9, 1981, abandoned.

[30] Foreign Application Priority Data

Aug. 2, 1980 [DE] Fed. Rep. of Germany ....... 3029426

[51] Int. Cl.$^5$ ..................... A01N 65/00; A01N 37/34
[52] U.S. Cl. ........................................ 514/65; 514/521
[58] Field of Search ................ 424/305, 308; 514/521, 514/65

[56] References Cited

U.S. PATENT DOCUMENTS

| | | | |
|---|---|---|---|
| 4,012,522 | 3/1977 | Searle et al. | 514/531 |
| 4,096,262 | 6/1978 | Andrews et al. | 424/250 |
| 4,130,655 | 12/1978 | Drabek et al. | 424/305 |
| 4,255,447 | 3/1981 | Ozawa et al. | 514/521 |
| 4,276,306 | 6/1981 | Fuschs et al. | 424/304 |
| 4,297,371 | 10/1981 | Fuchs et al. | 514/521 |

FOREIGN PATENT DOCUMENTS

| | | |
|---|---|---|
| 2757768 | 6/1978 | Fed. Rep. of Germany . |
| 2730515 | 1/1979 | Fed. Rep. of Germany . |
| 1425810 | 2/1976 | United Kingdom . |
| 2031417A | 4/1980 | United Kingdom . |
| 2038817A | 7/1980 | United Kingdom . |
| 2050169 | 1/1981 | United Kingdom . |
| 2058569 | 4/1981 | United Kingdom . |
| 1592056 | 7/1981 | United Kingdom . |
| 2065475 | 7/1981 | United Kingdom . |

OTHER PUBLICATIONS

Insektizide, 1975, Dr. H. Adophi, BASF.
The Ixodicidal Efficacy of a Number of Pour-on Formulations—on Housed Calves—K. Allan and B. H. Palmer.
Humko Chemical Products.
Matthewson, "European Patent Application", #0 005 826, 12-12-79.
WPI Accession No. 78-48175A/27, Acaricide Compsn. Effective Against Ixodoidea and Sarcoptiformes—Contains a Pyrethroid and an Organo-Phospharous Cpd.
DE 1542752-A, *Derwent Abstract*, 1970, AN 84-183182/30.

*Primary Examiner*—F. T. Moezie
*Attorney, Agent, or Firm*—Sprung Horn Kramer & Woods

[57] ABSTRACT

The invention relates to liquid pour-on formulations containing compounds active against ticks. The formulations contain in addition to the active material, a spreading oil, a solvent tolerated by skin and, optionally further auxiliaries.

6 Claims, No Drawings

… …

POUR-ON FORMULATIONS WHICH ARE ACTIVE AGAINST TICKS

This is a continuation of application Ser. No. 06/821,088, filed Jan. 21, 1986, which is a continuation of Ser. No. 06/595,083, filed Mar. 30, 1984, which is a continuation of Ser. No. 06/281,616, filed Aug. 9, 1981, now all abandoned.

The invention relates to certain new liquid pour-on formulations of active compounds with an action on ticks. The formulations according to the invention have a better activity than the pour-on formulations hitherto known for this application.

A pour-on formulation is characterised in that the active compound is dissolved, emulsified or suspended in a suitable solvent or solvent mixture which is tolerated by skin, if appropriate with the addition of further auxiliaries, and is applied with the aid of a suitable device (for example with the aid of a measuring beaker, a spray-bottle or a metering syringe) to the skin of the animal to be treated.

Pour-on formulations of insecticides and anthelmintic agents have already been disclosed in veterinary medicine (in this context, see W. M. Rogoff and P. H. Kohler, J. Econ. Ent. 53, 814–817 (1960)). The expression "pour-on formulation" or "spot-on formulation" is familiar to the expert. Such a formulation is a liquid preparation which is suitable for so-called "pour-on application" and is poured onto the skin (pour-on treatment).

For example, systemic phosphoric acid esters, such as Ruelene, trichlorphon and fenthion, which have a highly pronounced insecticidal action are used in the form of pour-on formulations for combating warble fly larvae.

However, it has not hitherto been possible to combat ticks with the required success by this method. Such pour-on formulations indeed showed a certain action, but this was inadequate by far. However, it is necessary in Africa, in particular, to achieve virtually 100% action on ticks, since otherwise the protozoonoses transmitted by ticks (for example East Coast fever) can still occur. Thus, in Africa, ticks are still combated in the conventional manner by dips or by spraying with aqueous active compound emulsions or suspensions.

According to the present invention there is provided a pour-on formulation of a compound which is active against ticks which formulation contains 0.1 to 30, preferably 0.5 to 20, parts by weight of the said active compound which is effective on ticks, 7 to 80, preferably 20 to 70, parts by weight of one or more spreading oils, 20 to 95 parts by weight of one or more solvents which are tolerated by skin and 0 to 20 parts by weight of further auxiliaries. The formulations according to the present invention effect very good distribution, over the skin of the animal, of the substance which is active against ticks.

Such a method of combating ticks by the "pour-on" process has the following advantages, compared with the conventional methods:

1. Expensive installation of a dip unit or spray unit is dispensed with.
2. There are not the difficulties of supplying water to dips and sprays and of supplying energy to spray units.
3. Driving the animals over long distances is dispensed with - and the animals thereby suffer no associated loss in weight.
4. There are not the difficulties in maintaining the optimum concentration of active compound in the dips. (When the animals are dipped, they withdraw an overproportional amount of active compound from the dip liquid ("stripping"). Additional active compound concentrate must thus be added to the dip at certain intervals, so that the active compound content in the dip does not fall below the dose which is still effective).

The pour-on formulations according to the invention exhibit virtually 100% action, and are comparable to the dip treatment and spray treatment with regard to their action. This is all the more remarkable since the pour-on process according to the invention can also be used in the case of substances which do not have a systemic action (oral and intravenous administration of the active compounds used showed no tickicidal action). For example, synthetic pyrethroids which have an action on ticks can be used as pour-on formulations in the dip process and spray process, in order to combat ticks.

It is surprising that such a low volume of such a formulation can become distributed over such a large surface area such as, for example, cattle have. This can be seen from the examples given below.

Possible active compounds which can be employed for the preparation of the pour-on formulations according to the invention are, above all: synthetic pyrethroids as described in German Offenlegungsschriften Nos. 27 30 515, corresponding to U.S. Pat. No. 4,276,306 dated June 30, 1981, 27 57 769 and 27 57 768, amidines or thioureas.

By spreading oils there are understood those oily liquids which distribute themselves particularly readily on the skin. They are known as such in cosmetics. According to a proposal by R. Reymer, Pharm. Ind. 32, 577 (1970) they can be characterised, for example, by their surface tension at an air interface, which, according to this proposal, should be less than 30 dynes/cm. This spreading property can also be determined experimentally by the so-called dab-off test on human skin (for example in R. Reymer, Pharm. Ind. 32, 577 (1970), or F. Neuwald, K. E. Fetting and A. Szakall, Fette-Seifen-Anstrichmittel 64, 465 (1962)).

Possible spreading oils are virtually any of the substances which have the abovementioned properties. The following classes of compounds and compounds are particularly suitable:

Silicone oils of various viscosities;

Fatty acid esters, such as ethyl stearate, di-n-butyl adipate, lauric acid hexyl ester, dipropylene glycol pelargonate, esters of a branched fatty acid of medium chain length and saturated $C_{16}$–$C_{18}$-fatty alcohols, isopropyl myristate, isopropyl palmitate, caprylic/capric acid esters of saturated fatty alcohols with a chain length of $C_{12}$–$C_{18}$, isopropyl stearate, oleic acid oleyl ester, oleic acid decyl ester, ethyl oleate, lactic acid ethyl ester, wax-like fatty acid esters, such as synthetic anatine uropygial gland fat, dibutyl phthalate, adipic acid diisopropyl ester and ester mixtures related to the latter;

Triglycerides, such as caprylic/capric acid triglyceride, triglyceride mixtures with vegetable fatty acids with a chain length of $C_8$–$C_{12}$ or other specifically chosen naturally occurring fatty acids, mixtures of partial glycerides of saturated or unsaturated fatty acids which may also contain hydroxyl groups and mono- and/or di-glycerides of the $C_8$/$C_{10}$-fatty acids;

Fatty alcohols, such as isotridecyl alcohol, 2-octyl-dodecanol, cetyl stearyl alcohol and oleyl alcohol; and Fatty acids, such as oleic acid.

Spreading oils which are particularly suitable are the following: isopropyl myristate, isopropyl palmitate, caprylic/capric acid esters of saturated fatty alcohols with a chain length of $C_{12}$–$C_{18}$, wax-like fatty acid esters, such as synthetic anatine uropygial gland fat, and silicone oils.

Possible solvents which are suitable for the preparation of the pour-on formulations according to the invention are in principle any of the inert organic and inorganic solvents which take up the tickicidally active substance in a sufficient concentration and do not damage tissue.

Particularly suitable solvents which can be used for the preparation of the pour-on formulations according to the invention are:

Alkanols, such as ethyl alcohol, isopropyl alcohol, n-butyl alcohol, amyl alcohol and octanol;

Glycols, such as propylene glycol, butylene 1,3-glycol, ethylglycol and dipropylene glycol monomethyl ether;

Aromatic alcohols, such as benzyl alcohol;

Carboxylic acid esters, such as ethyl acetate, benzyl benzoate, butyl acetate, propylene carbonate and lactic acid ethyl ester;

Aliphatic hydrocarbons;

Oils, which do not fall within the definition of the "spreading oils", such as cottonseed oil, ground nut oil, maize oil, olive oil, caster oil and sesame oil;

Water; and

Ketones, such as acetone and methyl ethyl ketone.

Furthermore, compounds such as dimethylsulphoxide, dimethylacetamide, dimethylformamide, N-methylpyrrolidone, dioxane and 2-dimethyl-4-hydroxyethyl-1,3-dioxalane, inter alia, are particularly suitable as solvents.

Alcohols with up to 8 carbon atoms in the molecule and ketones with up to 8 carbon atoms in the molecule, such as methyl ethyl ketone, and ethers (especially mono- or di -$C_1$-$C_2$- alkyl ethers) of ethylene glycol are especially suitable as solvents.

One or more solvents can be employed in the preparation of the pour-on formulations according to the invention.

Further auxiliaries which are suitable are:
a) adhesion promoters, for example carboxymethylcellulose, methylcellulose and other cellulose derivatives and starch derivatives, polyacrylates, alginates, gelatin, gum arabic, polyvinylpyrrolidone, polyvinyl alcohol, copolymers of methyl vinyl ether and maleic anhydride, polyethylene glycols, paraffins, oils, waxes and hydrogenated castor oil, colloidal silicic acid or mixtures of the substances mentioned.

Solutions and emulsions can contain, in addition to the active compound, the customary excipients, such as
b) surface-active agents (comprising emulsifiers and wetting agents), for example
1. anionic surface-active agents, such as Na lauryl sulphate, fatty alcohol ether-sulphates and monoethanol-amine salts of mono-/di-alkylpolyglycol ether orthophosphoric acid esters,
2. cationic surface-active agents, such as cetyltrimethylammonium chloride,
3. ampholytic surface-active agents, such ad di-Na-N-lauryl, iminodiproprionate or lecithin, and
4. non-ionic surface-active agents, for example polyoxyethylated casteroil, polyoxyethylated sorbitane monooleate, sorbitane monostearate, ethyl alcohol, glycerol mono-stearate, polyoxyethylene stearate and alkylphenol polyglycol ethers.
c) Stabilisers for preventing the chemical degradation which occurs in the case of some active compounds, such, as, for example, antioxidants, for example tocopherols and butylhydroxyanisole.

The pour-on formulations according to the invention may have the following composition:
a) Active compound: 0.1 to 30 percent by weight, preferably 0.5 to 20 percent by weight.
b) Spreading oil: 7 to 80 percent by weight, preferably 20–70 percent by weight.
c) Solvent: 20 to 95 percent by weight, preferably 60 to 90 percent by weight.
d) Further auxiliaries: 0 to 20 percent by weight, preferably 0 to 10 percent by weight.

Preferred pour-on formulations according to the invention have the following composition:

active compound(s): 0.5 to 20 percent by weight (preferably 1 to 10 percent by weight);

spreading oil(s) selected from isopropyl myristate, isopropyl palmitate, caprylic/capric acid triglyceride, saturated triglycerides of naturally occurring fatty acids, fatty acid esters which correspond to synthetic anatine uropygial gland fat and silicone oils: 7 to 80 percent by weight (preferably 20 to 70 percent by weight); and solvent(s) selected from isopropanol, amyl alcohol, methyl ethyl ketone, glycol ethers, butyl acetate and lactic acid ethyl ester: 20 to 95 percent by weight (preferably 60 to 90 percent by weight).

The present invention also includes pour-on formulations in dosage unit form.

"Pour-on formulation in dosage unit form" as used in this Specification means physically discrete coherent units suitable for administration each containing a daily dose or a multiple (up to four times) or submultiple (down to a forthieth) of a daily dose of the active compound of the invention. Whether the formulation contains a daily dose or, for example, a half, a third or a quarter of a daily dose will depend on whether the formulation is to be administered once or, for example, twice, three times or four times a day respectively.

Solutions, suspensions, emulsions and sprays may be mentioned as preferred pharmaceutical formulations.

The pour-on formulations according to the invention are prepared by dissolving, emulsifying or suspending the substance which is active against ticks in a suitable solvent or solvent mixture which is tolerated by the skin, adding spraying oils and, if appropriate, adding the other auxiliaries.

The above sequence of process steps is not critical and can be changed, or the constituents of the pour-on formulations according to the invention can also be brought together, if appropriate, simultaneously, whilst stirring continuously. During the preparation, the individual constituents are added in the abovementioned proportions.

The formulations according to the invention which are listed below have been prepared as described above, and their activity has been tested in comparison with formulations which did not contain spreading oils.

The present invention also provides a method of freeing or protecting domesticated animals from ticks which comprises applying to said animals a pour-on formulation according to the present invention, in admixture with a diluent or carrier.

The present invention further provides domesticated animals whenever freed or protected from ticks by the application to said animals of a pour-in formulation according to the present invention, in admixture with a diluent or carrier.

The superior activity of the formulations according to the invention is illustrated by the following biotest-Examples.

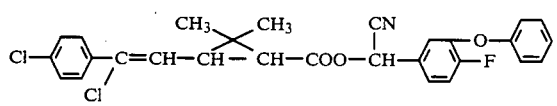

5 parts of the active compound of the formula (I) were dissolved in 95 parts of a mixture of solvents and spreading agents.

The resulting active compound formulation was poured onto cattle which had been infected with resistant tick larvae of the species Boophilus microplus, Biarra strain (12 repeated infections at intervals of 2 days).

The action of the active compound formulation was determined by ascertaining the number of adult female ticks which developed on the treated cattle. This number was compared with the number of adult female ticks which developed on untreated cattle. A compound was the more active, the fewer female ticks developed after the treatment.

The number of adult females which, in treated and untreated animals, developed in the last three days before the time of treatment was used as a measure of the severity of the infection before treatment.

EXAMPLE A

*Boophilus microplus* (Biarra strain, resistant): all stages of development (cattle) formulation according to the invention (as described in Example 1): activity in % in the pour-on process

| Dose of active compound in mg/kg | Action in % | | | |
|---|---|---|---|---|
| | 1st–6th day A (Adult) | 7th–15th day MN-N (methanympho-nymphs) | 16th–21st day ML-L (metalarvae: larvae) | 1st–21st day all stages |
| 5 | 100 | 100 | 100 | 100 |
| 2,5 | 100 | 100 | 100 | 100 |
| 1 | 100 | 100 | 100 | 100 |
| 0,5 | 99,6 | 99,98 | 100 | 99,84 |
| 0,25 | 99,83 | 100 | 100 | 99,95 |
| 0,1 | 99,7 | 99,1 | 61,8 | 88,06 |

EXAMPLE B

*Boophilus microplus* (Biarra strain, resistant): all stages of development (cattle) known formulation of the pyrethroid of the formula (I): activity in % in the pour-on process

| Dose of active compound in mg/kg | Action in % | | | |
|---|---|---|---|---|
| | 1st–6th day A | 7th–15th day MN-N | 16th–21st day ML-L | 1st–21st day all stages |
| 5 | 100 | 100 | 100 | 100 |
| 2,5 | 99,8 | 99,7 | 99,9 | 94,8 |
| 1,0 | 98,9 | 96,4 | 98,9 | 98,7 |
| 0,5 | 94,3 | 81,6 | 95,0 | 89,0 |

For comparison: 1 mg/kg of the pyrethroid of the formula (I) showed no action on ticks when administered intravenously. Accordingly, no systemic action of the substance occurred.

The following Examples 1 to 3 illustrate formulations according to the present invention.

EXAMPLE 1

| Active compound of the formula (I) | 5.00 g |
|---|---|
| Isopropyl myristate | 30.00 g spreading |
| 2-Octyl-dodecanol | 20.00 g oils |
| Isopropyl alcohol | 28.75 g |
| 100 ml = | 83.75 g |

The substances are weighed together and stirred, until a clear solution has formed.

EXAMPLE 2

The composition of the formulation corresponded to that in Example 1 and was prepared similarly.

The proportion of active compound of the formula (I) was 0.5%.

The activity at a dose of 0.25 mg/kg was likewise 100 percent.

EXAMPLE 3

| Example 3 | |
|---|---|
| Active compound as in Example 1 | 0.50 g |
| Silicone oil | 30.00 g |
| Butyl acetate | 59.42 g |
| 100 ml = | 89.92 g |

The formulation was prepared similarly to Example 1.

At 0.25 mg/kg, this formulation was 100% effective. In contrast, the activity of a comparison formulation containing no silicone oil was only 80% at the same dosage.

As a commercially available spot-on formulation for combating warble flies, a fenthion pour-on formulation has an action against ticks of only 85%.

What is claimed is:

1. A pour-on formulation which is active against ticks, and which effects distribution over the skin of an animal to which it is applied the active ingredient consisting of 0.1 to 30 parts by weight of a compound having no systemic action of the formula

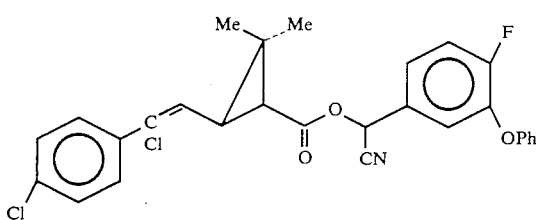

10 to 80 parts by weight of a spreading oil, wherein said spreading oil has a surface tension at an air interface which is less than 30 dynes/cm and, 20 to 95 parts by weight of at least one solvent which is tolerated by the skin of an animal to which the formulation is applied.

2. A pour-on formulation of claim 1, which contains 0.1 to 20 parts by weight of the active compound, 10 to 70 parts by weight of the spreading oil and 20 to 95 parts by weight of the solvent.

3. A pour-on formulation according to claim 1, wherein the spreading oil is isopropyl myristate, isopropyl palmitate, a mixture of caprylic and capric acid esters of a saturated alcohol with a chain length of $C_{12}$–$C_{18}$, or a silicone oil.

4. A pour-on formulation according to claims 1 wherein the solvent is an alcohol with up to 8 carbon atoms in the molecule or a mono- or di-$C_1$-$C_2$-alkyl ether of ethyleneglycol.

5. A pour-on formulation according to claim 1 containing active compounds: 0.5 to 20 percent by weight; spreading oil selected from the group consisting of isopropyl myristate, isopropyl palmitate and a saturated triglyceride of a naturally occurring fatty acid of at least 8 carbon atoms; and silicone oil: 10 to 80 percent by weight; and a solvent selected from the group consisting of isopropanol, amyl alcohol, methyl ethyl ketone, glycol ether, butyl acetate and lactic acid ethyl ester: 20 to 90 percent by weight.

6. A method of freeing or protecting domesticated animals from ticks, which comprises applying to said animals a pour-on formulation according to claim 1.

* * * * *